US00PP18071P2

(12) United States Plant Patent
Gunnison

(10) Patent No.: US PP18,071 P2
(45) Date of Patent: Sep. 25, 2007

(54) APPLE TREE NAMED 'GUN-300'

(50) Latin Name: ***Malus* Mill.**
Varietal Denomination: GUN-300

(76) Inventor: Hugh Gunnison, P.O. Box 477, Route 22, Crown Point, NY (US) 12928

( * ) Notice: Subject to any disclaimer, the term of this patent is extended or adjusted under 35 U.S.C. 154(b) by 0 days.

(21) Appl. No.: 11/089,051

(22) Filed: Mar. 23, 2005

Related U.S. Application Data

(60) Provisional application No. 60/556,395, filed on Mar. 24, 2004.

(51) Int. Cl.
*A01H 5/00* (2006.01)

(52) U.S. Cl. ..... Plt./165

(58) Field of Classification Search ..... Plt./165
See application file for complete search history.

*Primary Examiner*—Kent L. Bell
*Assistant Examiner*—Annette H Para
(74) *Attorney, Agent, or Firm*—Stratton Ballew PLLC

(57) ABSTRACT

A new and distinct apple tree named 'GUN-300' is disclosed. The fruit of 'GUN-300' is notable for its even, early coloring and firm flesh.

3 Drawing Sheets

Latin name of the genus and species of the plant claimed: *Malus* Mill.
Variety denomination: 'GUN-300'.

BRIEF DESCRIPTION OF THE PHOTOGRAPH

BACKGROUND OF THE INVENTION

Figure 1:
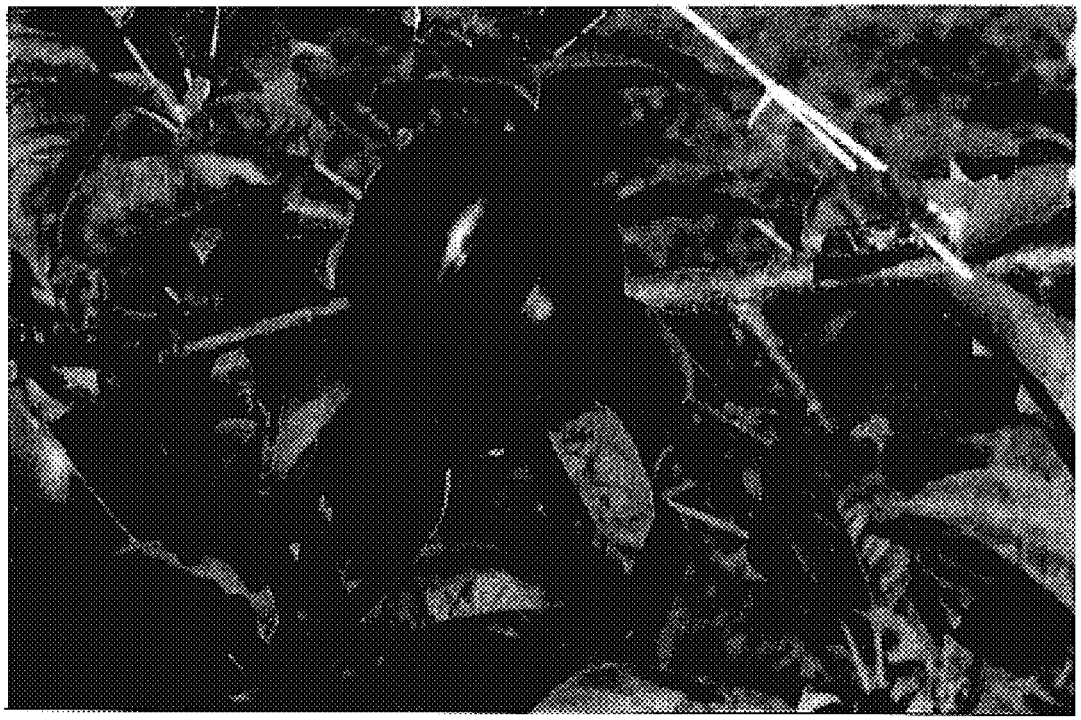
FIG. 1 shows the fruit and leaves of 'GUN-300'.
Figure 2:
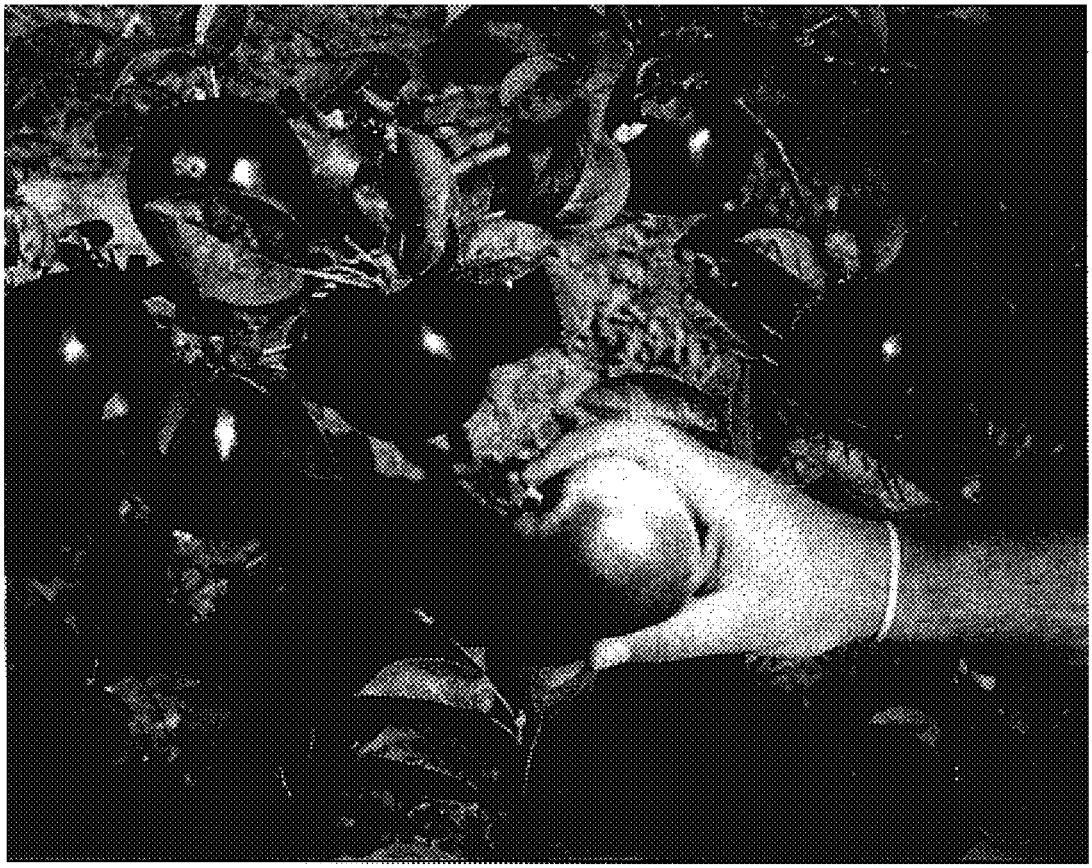
FIG. 2 shows several fruit and leaves of 'GUN-300' as compared to a fruit of 'Rogers Red McIntosh'.
Figure 3:
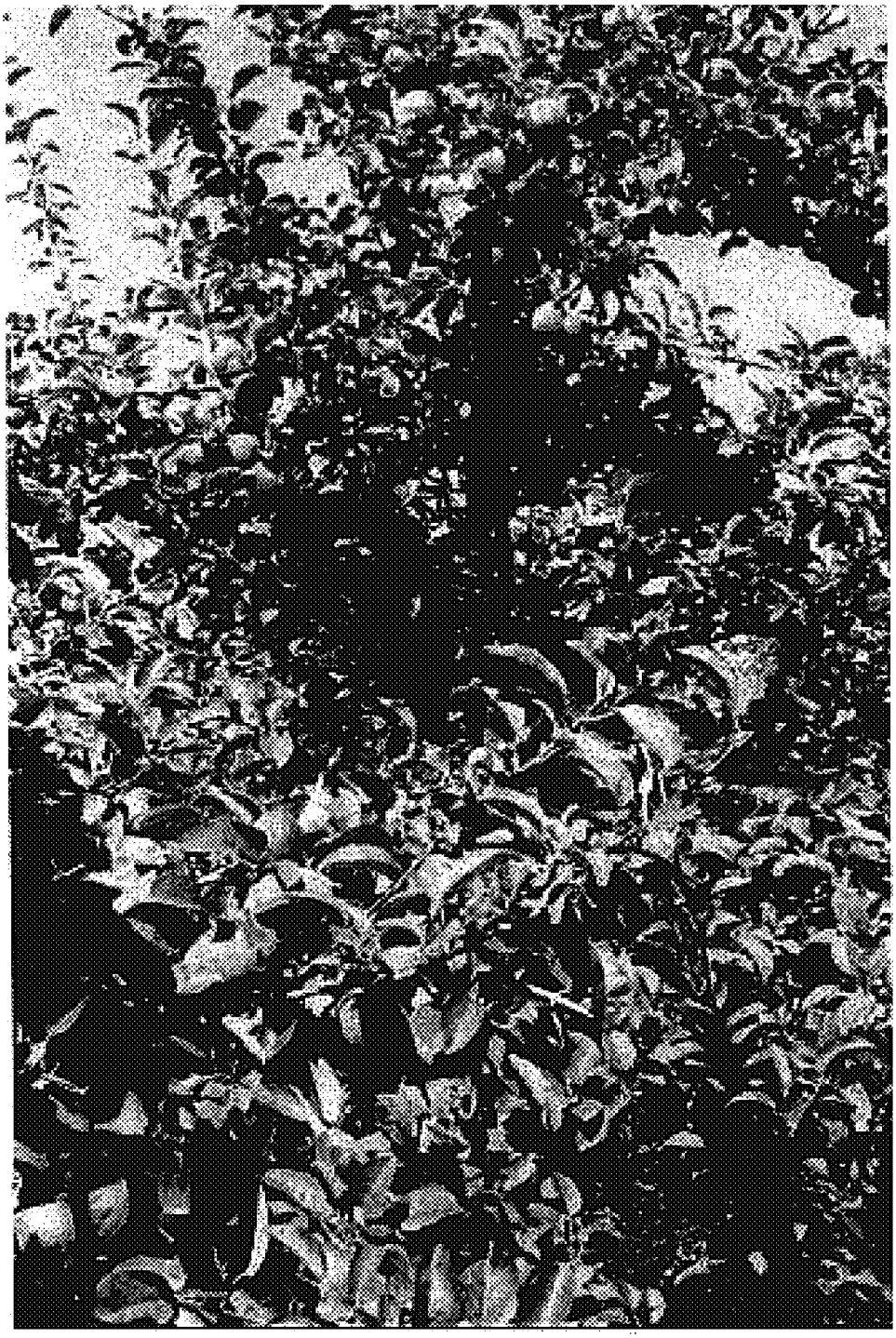
FIG. 3 shows the tree, branches, leaves and fruit of 'GUN-300'.

'GUN-300' is a new and distinct 'McIntosh' apple tree. It originated as a full tree mutation discovered near Crown Point, N.Y. in a cultivated area planted with 'Rogers Red McIntosh' (unpatented) trees, and was found to be distinguishable from 'Rogers Red McIntosh' and other known varieties. The new cultivar has been asexually propagated by budding and grafting near Louisana, Mo. and Hatford, Mich., and has been found to remain true to type through successive asexual propagations.

SUMMARY OF THE INVENTION

The limbs of the 'GUN-300' tree are substantially horizontal, compared to the more vertical branches of the 'Rogers Red McIntosh.' The fruit of 'GUN-300' is notable for its even, early coloring (10 to 14 days before 'Rogers Red McIntosh') and firm flesh (pressure is 1 to 2 pounds greater than 'Rogers Red McIntosh').

DETAILED BOTANICAL DESCRIPTION

The following is a botanical description of 'GUN-300', based on observations of seven year old specimens grown on M26 rootstock near Crown Point, N.Y., USA during the 2004 growing season. All colors are described according to The Royal Horticultural Society Colour Chart. It should be understood that the botanical features described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree— Medium vigor, comparable to other 'McIntosh' strains; non-spur type; Spreading, upright in form; Non-spur growth type; height about 2.5 m; bark smooth; trunk diameter about 7.0 cm at 30 cm above the graft union; trunk color brown 200B; lenticels small, sparse, few in number, white 155A.

Branches— Length of fruiting branch 0.9 m at 1 m above graft union; crotch angle nearly horizontal to slightly upright, 65 to 85 degrees; lenticels small, sparse, few in number, white 155A.

Winter hardiness— No winter injury observed; chilling requirement similar to 'Rogers Red McIntosh.'

Flowers— 3 to 5 flowers per cluster; 3.8 cm diameter.

Petals— 5 petals per flower; length 15 mm; Ovate, rounded base, rounded apex; Soft texture; Color pale pink 58C.

Bloom— First bloom May 12 to 15 at Crown Point, N.Y.; Full bloom May 15 (same as 'Rogers Red McIntosh').

Leaves— Ovate to oval; long, 70 mm, wide, 57 mm, medium length to width ratio; tip acuminate, base rounded; serrate margin; color of upper surface yellow-green 147A, lower surface green 138B; Petiole length 33 mm.

Fruit— Up to 3 to 4 per cluster; diameter 7.0 to 8.5 cm; height 6.3 cm; weight about 200 to 210 g; globose to ovate; ribbing minimal; eye closed; lenticels very small, few in number, 75% to 100% overcolor; skin over-color red 46B, base color yellow 2B; flesh color white 155A; 12.3 to 14.7° Brix at harvest; Seeds 7–10, length 6 mm, width 3 mm, color grayed-orange 175A; Harvest dates September 15–20 in Crown Point, N.Y.

It is claimed:

1. What is claimed is a new and distinct apple tree substantially as shown and described herein.

* * * * *